United States Patent [19]

Wessel

[11] Patent Number: 5,412,150
[45] Date of Patent: May 2, 1995

[54] PROCESS FOR THE PREPARATION OF METHYL 5-BROMO-6-METHOXY-1-NAPHTHOATE

[75] Inventor: Thomas Wessel, Maintal, Germany

[73] Assignee: Cassella AG, Frankfurt am, Germany

[21] Appl. No.: 247,595

[22] Filed: May 23, 1994

[30] Foreign Application Priority Data

Jun. 1, 1993 [DE] Germany ............... 43 18 069.8

[51] Int. Cl.⁶ .................................. C07L 69/76
[52] U.S. Cl. .......................................... 560/56
[58] Field of Search ............................. 560/56

[56] References Cited

U.S. PATENT DOCUMENTS

| | | | |
|---|---|---|---|
| 4,551,557 | 12/1984 | Ratton et al. | 568/433 |
| 4,739,100 | 9/1985 | Adrian et al. | 560/56 |
| 5,107,013 | 4/1992 | Cannata, V et al. | 560/56 |

FOREIGN PATENT DOCUMENTS

| | | |
|---|---|---|
| 35305 | 9/1981 | European Pat. Off. . |
| 59596 | 9/1982 | European Pat. Off. . |
| 0149407 | 12/1984 | European Pat. Off. . |
| 0200840 | 9/1985 | European Pat. Off. . |
| 200840 | 12/1986 | European Pat. Off. . |
| 245679 | 11/1987 | European Pat. Off. . |
| 307519 | 3/1989 | European Pat. Off. . |
| 3014972 | 4/1980 | Germany . |
| 61-171452 | 8/1986 | Japan . |

*Primary Examiner*—Paul J. Killos

[57] ABSTRACT

The present invention relates to a process for the preparation of methyl 5-bromo-6-methoxy-1-naphthoate by brominating methyl 6-methoxy-1-naphthoate with bromine, in which between 0.5 and 0.6 mol of bromine ($Br_2$) are employed per mole of methyl 6-methoxy-1-naphthoate and the bromination is carried out in the presence of an oxidant.

19 Claims, No Drawings

PROCESS FOR THE PREPARATION OF METHYL 5-BROMO-6-METHOXY-1-NAPHTHOATE

The present invention relates to a process for the preparation of methyl 5-bromo-6-methoxy-1-naphthoate by brominating methyl 6-methoxy-1-naphthoate with bromine in the presence of an oxidant.

Methyl 5-bromo-6-methoxy-1-naphthoate is an important intermediate in the preparation of the pharmaceutical active substance tolrestat, which is used for the prevention and treatment of late sequelae of diabetes mellitus. Tolrestat inhibits the enzyme aldose reductase and thus prevents the formation of sorbitol, which is increased in diabetics and which leads to, for example, kidney damage, nerve damage or damage to the eyes (see, for example, EP-B 059,596, EP-B 200,840, EP-A 307,519, U.S. Pat. No. 808,748).

The preparation of methyl 5-bromo-6-methoxy-1-naphthoate(I) by brominating methyl 6-methoxy-1-naphthoate(II) with bromine has been described.

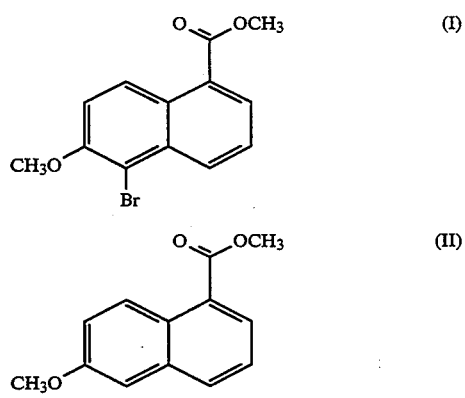

According to the process of EP-B 200,840, a large excess of bromine is employed and the reaction is carried out in the presence of water in 1,2-dichloroethane, a halogenated hydrocarbon which is a health hazard and under the suspicion of being carcinogenic and whose use in an industrial-scale synthesis is not acceptable with a view to ecology and industrial hygiene.

The bromination process described in EP-B 059,596 avoids the use of chlorinated hydrocarbons. Acetic acid is used as solvent. However, this process also employs an excess of bromine (1.2 mol of $Br_2$ per mole of methoxynaphthoate(II)). Moreover, this procedure requires subsequent purification by recrystallization from ethanol. The yield is only 81%, and the melting point of 119° C. which has been given suggests that the purity of the recrystallized product is low.

Both processes necessarily result in the formation of 1 mol of hydrogen bromide per mole of bromomethoxynaphthoate(I) formed, and this hydrogen bromide is dissolved in the filtrate or must be scrubbed out of the waste air, whereupon it is found in the waste water which must be subjected to an additional work-up step. Considerably less than half of the bromine employed is utilized in the preparation processes of the prior art caused by the formation of hydrogen bromide and the necessity of having to add substantially more than the equimolar amount of $Br_2$.

Bromination reactions is aromatic substances in which the hydrogen bromide formed from the bromine is converted back into bromine by addition of an oxidant have been disclosed. The German Patent Specification 748,621 discloses a process for the bromination of phenols and naphthols in phosphorus oxychloride, where an addition of an oxidant such as, for example, sulphur trioxide or oleum results in a virtually quantitative utilization of bromine. Dakka and Sasson, Journal of the Chemical Society, Chemical Communications, 1987, p. 1421, describe the bromination of benzene, alkylbenzenes and chlorobenzene with half the molar amount of $Br_2$ with an addition of aqueous hydrogen peroxide in the presence of a quaternary ammonium salt as phase transfer catalyst. However, the aromatic starting substances employed have no hydrolysable functional groups, such as ether and ester groups. In the case of bromination reactions of starting compounds which contain such groups, the formation of secondary products due to ester and ether cleavage is to be expected in the reaction medium, which is acidic due to the hydrogen bromide formed. To contain the secondary reactions, the bromination of phenol ethers and of esters of aromatic carboxylic acids frequently requires an addition of an agent which binds hydrogen bromide, such as sodium acetate or calcium carbonate (cf. Houben-Weyl-Müeller, Methoden der Organischen Chemie, [Methods in Organic Chemistry], Volume V/4, p. 246, p. 269, p. 291, Stuttgart 1960), and this addition makes the procedure more complicated, in particular on an industrial scale.

It is therefore the object of the present invention to provide a process for the preparation of methyl 5-bromo-6-methoxy-1-naphthoate(I), which is improved with a view to ecology and industrial hygiene, reduces pollution of the waste water, avoids the use of chlorinated hydrocarbons and gives high yields of an ultrapure product using a simple procedure.

Surprisingly, it has been found that this object can be achieved by brominating the methoxynaphthoate(II) with 0.5 mol or a negligible excess of $Br_2$ per mole of the ester II in the presence of an oxidant which is capable of oxidizing hydrogen bromide to give bromine and thus regenerating the hydrogen bromide which is necessarily formed in the electrophilic aromatic bromination reaction.

The present invention therefore relates to a process for the preparation of methyl 5-bromo-6-methoxy-1-naphthoate(I) by brominating methyl 6-methoxy-1-naphthoate(II) with bromine, characterized in that between 0.5 and 0.6 mol of bromine ($Br_2$) are employed per mole of methyl 6-methoxy-1-naphthoate(II) and in that the bromination is carried out in the presence of an oxidant which is capable of oxidizing hydrogen bromide to give bromine. Depending on how the bromination is carried out, it is also possible to employ, for example, $Br_2$ in amounts of 0.55 to 0.52 mol per mole of methyl 6-methoxy-1-naphthoate(II). Examples of oxidants which, under the prevailing reaction conditions, are capable of reoxidizing hydrogen bromide to give bromine and which do not react unfavourably with the starting material and the product are manganese dioxide, cerium(IV) salts, alkali metal bromates or peroxy compounds; the bromide can also be reoxidized electrochemically.

The oxidant preferably employed in the process according to the invention is a peroxy compound. Peroxy compounds are to be understood as meaning in this case, besides hydrogen peroxide itself, the inorganic and organic derivatives thereof in which one of the two hydrogen atoms, or both, are replaced by covalently bonded radicals or by ionically bonded cations. Suitable ionically bonded cations are above all the cations of the alkali metals and alkaline earth metals, in particular sodium and barium, and suitable covalently bonded radicals are, for example, trialkylsilyl radicals, alkyl radicals, acyl radicals which are derived from aliphatic or aromatic carboxylic acids, sulphonyl radicals or radicals of inorganic acids. Examples of peroxy compounds which can be employed according to the invention under the prevailing reaction conditions are sodium peroxide and barium peroxide and their hydrates, bis-trimethylsilyl peroxide, tert.-butyl hydroperoxide, peroxyformic acid, peroxyacetic acid, peroxypropionic acid, peroxylauric acid, peroxystearic acid, peroxytrifluoroacetic acid, peroxybenzoic acid, m-chloroperoxybenzoic acid and monoperoxyphthalic acid, and their alkali metal salts and alkaline earth metal salts, the so-called alkali metal perborates and alkali metal percarbonates, such as sodium perborate and sodium percarbonate, peroxomonosulphuric acid, peroxodisulphuric acid, sodium peroxodisulphate, potassium peroxodisulphate and ammonium peroxodisulphate, potassium peroxomonosulphate, also in the form of its addition compounds with potassium sulphate and potassium hydrogen sulphate, peroxomonophosphoric acid and peroxodiphosphoric acid and their sodium and potassium salts, or peroxonitric acid, it being possible for the peroxy compounds not only to be employed in the process according to the invention in substance or in the form of commerically available preparations, but also to be formed, or prepared, in situ just before or while the process according to the invention is carried out.

The oxidant which is particularly preferably employed in the process according to the invention is hydrogen peroxide. Advantageously used are, in particular, commerically available aqueous hydrogen peroxide solutions in the concentration range from 20 to 50% by weight, such as, for example, the 30%, 35% or 40% solution. However, adducts of hydrogen peroxide can also be employed, for example the adduct with urea or the adducts with sodium borates or sodium carbonate. In particular, when hydrogen peroxide itself is used, the only waste product of the process according to the invention is water, as shown by the reaction equation which follows.

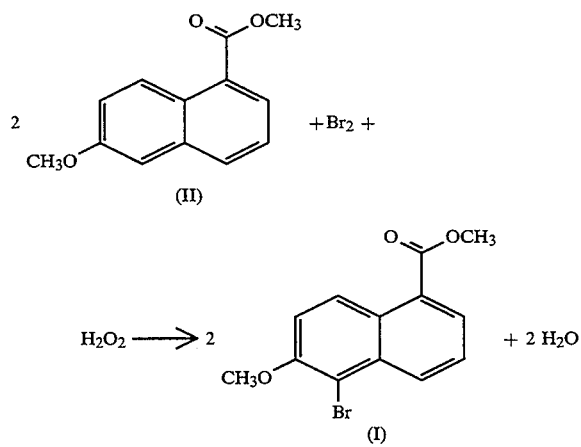

The hydrogen bromide formed can be reoxidized not only with individual substances but also using mixtures of oxidants which are capable of oxidizing hydrogen bromide to give bromine. Equally, the peroxy compounds which are preferred as oxidants can be employed in the form of mixtures of two or more peroxy compounds, or they can be formed, or exist, in the form of such mixtures when the process is carried out. This also applies to hydrogen peroxide which is particularly preferred and which can be employed, or exist, in the form of a mixture with one or more other peroxy compounds.

The sequence in which the reactants are combined can be varied. For example, the methoxynaphthoate(II) can initially be introduced together with the oxidant and the bromine can be metered in-for example in the course of 30 to 90 minutes in the case of a laboratory-scale 1-mol batch-, or the ester II can initially be introduced and first the bromine and then the oxidant can be metered in, or the bromine and the oxidant can also be metered simultaneously into the ester II. The amount of oxidant required depends on the reaction procedure. To reoxidize the hydrogen bromide to give bromine, the oxidant must provide at least one redox equivalent per mole of methoxynaphthoate(II). An excess of oxidant is frequently employed to achieve a complete and rapid reoxidation reaction. If hydrogen peroxide is used as the oxidant, it can be expedient to use an equimolar to 1.2-fold molar amount relative to the methyl 6-methoxy-1-naphthoate(II); preferably between 0.5 and 0.8 mol, particularly preferably between 0.55 and 0.7 mol, of hydrogen peroxide are employed per mole of II.

Depending on the reaction conditions and the oxidant, a range of solvents, by themselves or in the form of a mixture, can be suitable for carrying out the process according to the invention, for example hydrocarbons, ethers, alcohols, carboxylic acids, carboxamides or water. The reaction is preferably carried out in a solvent which is miscible with water. In this case, no second liquid phase is present either when the oxidant is employed in the form of an aqueous solution, when the solubility requirements, such as those of salts, require an addition of water, or when the addition of auxiliaries, such as acids, is necessary. Also in such a case, the product can immediately be washed with water, which can be handled without problems, to remove attached filtrate and salts which may be present. Examples of suitable solvents which are miscible with water are lower aliphatic carboxylic acids, such as formic acid, acetic acid or propionic acid, lower aliphatic alcohols, such as methanol, ethanol, propanol or isopropanol, ethylene glycol and its water-miscible ethers, such as ethylene glycol monomethyl ether and ethylene glycol dimethyl ether, diethylene glycol, diethylene glycol monomethyl ether and diethylene glycol dimethyl ether, tetrahydrofuran, dioxane, carboxamides, such as dimethylformamide and N-methylpyrrolidone. A substance which is particularly preferred as solvent is a lower aliphatic carboxylic acid or a lower aliphatic alcohol. The use of acetic acid or methanol as solvent is very particularly preferred. The amount of solvent depends on the reaction conditions. The ratio by weight of 6-methoxy-1-naphthoate(II) to solvent can be, for example, 1:2 to 1:20, but, depending on the embodiment, the ratio can be, for example, 1:3 to 1:7 and, in particular, 1:4 to 1:6. This applies especially to the use of acetic acid.

Depending on how the reaction is conducted, the process according to the invention can be carried out under cold or warm conditions. The reaction is preferably carried out between 0° C. and the boiling point of the reaction mixture, in particular between room temperature and the boiling point. A range of temperatures can be set in the course of the reaction, for example it is possible to first maintain a temperature between 0° C. and 50° C., preferably between room temperature and 45° C., particularly preferably between 30° C. and 40°C., during the metering-in process, and, when the addition has ended, the temperature of the reaction mixture can subsequently be increased to allow residues of the starting substance II to be reacted more rapidly to completion, for example at 70° C. or 90° C. or up to the boiling point. Moreover, crystallization of the product upon cooling of the hot solution when the reaction is complete entails a purification effect.

The product can be isolated by customary working-up methods. If the product is only sparingly soluble in the solvent used, the crystallized substance is first cooled, for example to 30° C. or 20° C. or 0° C., and then separated by filtration or centrifugation, washed and dried. If the solubility of the product is higher, part of the solvent may be distilled off under atmospheric pressure or in vacuo before the crystallizate is cooled and removed.

The process according to the invention gives methyl 5-bromo-6-methoxy-1-naphthoate(I) in a high yield of approximately 90% and with the high purity of >98% (GC content) so that an additional recrystallization step for further processing can be dispensed with. This could not have been predicted by a person skilled in the art. As explained above, it was to be expected from the prior art that secondary products from ether cleavage and ester hydrolysis would result in losses, especially since it was known that purity suffers in the transition from 1,2-dichloroethane as solvent, in which the hydrogen bromide with its cleaving activity is only sparingly soluble, to acetic acid, in which hydrogen bromide is readily soluble. The good result obtained by the process according to the invention is all the more surprising bearing in mind that it is possible for water to be present. Considerable advantages with a view to industrial hygiene, ecology and economy are obtained by the fact that chlorinated hydrocarbons can be dispensed with as solvents and because the waste water and the waste air are no longer polluted with hydrogen bromide because the amount of bromine is greatly reduced. The following table shows the improvement which Example 1 (bromination in acetic acid) of the present invention represents when compared with the most similar prior art, i.e. the bromination reaction of the ester II in acetic acid as described in EP-B 059,596 in Example 1 g therein.

|  | according to the invention | prior art |
|---|---|---|
| Mol of Br$_2$ per mole of II | 0.52 | 1.20 |
| Theoretical amount of hydrogen bromide formed (mol) per mole of I | 0 | 1 |
| Additional recrystallization step | no | yes |
| Yield | 92.5% | 81% |
| Melting point | 126–127.5° C. | 119° C. |

EXAMPLES

1. Bromination in Acetic Acid 108 g (0.50 mol) of methyl 6-methoxy-1-naphthoate are dissolved in 500 ml of acetic acid, and 30 g of 35% aqueous hydrogen peroxide solution are added. 42 g (0.26 mol) of bromine are then added dropwise at 35° C. in the course of 45 minutes. The mixture is subsequently heated at 90° C. When the reaction has ended, the mixture is allowed to cool to 20° C. and is subjected to filtration with suction, and the filter cake is washed with water. Drying in vacuo at 60° C. gives 136.1 g of methyl 5-bromo-6-methoxy-1-naphthoate in the form of fine white needles.
Yield: 92.5%
Purity: >98% (GC)
Melting point: 126°–127.5° C.

2. Bromination in Methanol 108 g (0.50 mol) of methyl 6-methoxy-1-naphthoate are dissolved in 2500 ml of methanol, and 30 g of 35% hydrogen peroxide solution are added. 42 g (0.26 mol) of bromine are then added dropwise at 35° C. in the course of 60 minutes. The mixture is subsequently heated at 70° C. When the reaction has ended, the mixture is concentrated in vacuo to a total volume of approximately 500 ml, allowed to cool to 20° C. and subjected to filtration with suction, and the filter cake is washed with methanol and water. Drying in vacuo at 60° C. gives 128.0 g of methyl 5-bromo-6-methoxy-1-naphthoate in the form of fine white needles.
Yield: 87.1%
Purity: >98% (GC)
Melting point: 125.5°–127° C.

I claim:
1. Process for the preparation of methyl 5-bromo-6-methoxy-1-naphthoate of formula (I)

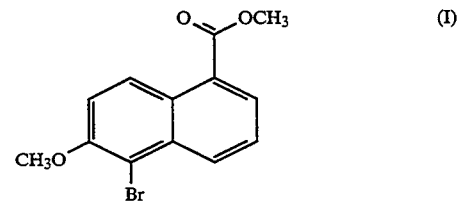

comprising brominating methyl 6-methoxy-1-naphthoate of formula (II)

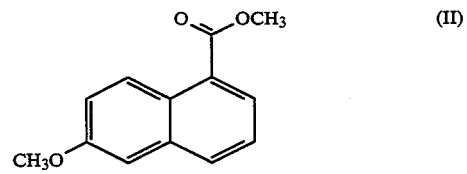

with bromine, wherein between about 0.5 and 0.6 mol of bromine (Br$_2$) are employed per mole of methyl 6-methoxy-1-naphthoate and carrying out the bromination in the presence of an oxidant which is capable of oxidizing hydrogen bromide to give bromine.

2. Process according to claim 1, wherein the oxidant employed is a peroxy compound.

3. Process according to claim 2, wherein the peroxy compound is selected from the group consisting of inorganic or organic derivatives of hydrogen peroxide in which one of the two hydrogen atoms of the hydrogen peroxide, or both, are replaced by covalently bonded radicals or by ionically bonded cations.

4. Process according to claim 1, wherein the oxidant employed is hydrogen peroxide.

5. Process according to claim 4, wherein between 0.5 and 0.8 mol of hydrogen peroxide are employed per mole of methyl 6-methoxy-1-naphthoate.

6. Process according to claim 4, wherein between 0.55 and 0.70 mol of hydrogen peroxide are employed per mole of methyl 6-methoxy-1-naphthoate.

7. Process as claimed in claim 1, wherein between 0.52 to 0.55 mols of bromine are employed per mol of methyl 6-methoxy-1-naphthoate.

8. Process according to claim 1, wherein the reaction is carried out in a solvent which is miscible with water.

9. Process as claimed in claim 8, wherein the solvent is selected from the group consisting of lower aliphatic carboxylic acids, lower aliphatic alcohols, water-miscible ethers, tetrahydrofurane, dioxane, carboxamides and mixtures thereof.

10. Process according to claim 8, wherein the solvent used is a lower aliphatic carboxylic acid or a lower aliphatic alcohol.

11. Process according to claim 8, wherein the solvent used is acetic acid.

12. Process according to claim 8, wherein the solvent used is methanol.

13. Process according to claim 1, wherein the reaction is carried out between 0° C. and the boiling point of the reaction mixture.

14. Process according to claim 1, wherein the reaction is carried out between room temperature and the boiling point.

15. Process according to claim 4, wherein the hydrogen peroxide is in a solution having a concentration range from 20 to 50% by weight.

16. Process according to claim 15, wherein the hydrogen peroxide has a concentration range from 30 to 40% by weight.

17. Process as claimed in claim 8, wherein the ratio by weight of formula II to solvent is 1:2 to 1:20.

18. Process as claimed in claim 17, wherein the ratio by weight of formula II to solvent is 1:3 to 1:7.

19. Process as claimed in claim 17, wherein the ratio by weight of formula II to solvent is 1:4 to 1:6.

* * * * *